United States Patent
Thoreson et al.

(10) Patent No.: US 11,026,719 B2
(45) Date of Patent: Jun. 8, 2021

(54) RADIALLY EXPANDABLE INTRODUCER SHEATH

(71) Applicant: BOSTON SCIENTIFIC SCIMED, INC., Maple Grove, MN (US)

(72) Inventors: Michael Richmon Thoreson, Maple Grove, MN (US); Adam David Grovender, Maple Grove, MN (US); Scott Solberg, Ramsey, MN (US); David Raab, Roseville, MN (US); Benjamin Philip Gundale, Plymouth, MN (US); Ross A. Olson, Anoka, MN (US); James M. Anderson, Corcoran, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 231 days.

(21) Appl. No.: 15/979,703

(22) Filed: May 15, 2018

(65) Prior Publication Data
US 2018/0325549 A1 Nov. 15, 2018

Related U.S. Application Data

(60) Provisional application No. 62/506,239, filed on May 15, 2017.

(51) Int. Cl.
*A61B 17/34* (2006.01)
*A61M 25/06* (2006.01)
(Continued)

(52) U.S. Cl.
CPC ...... *A61B 17/3468* (2013.01); *A61B 17/3423* (2013.01); *A61B 17/3439* (2013.01);
(Continued)

(58) Field of Classification Search
CPC . A61B 17/34; A61B 17/3243; A61B 17/3439; A61B 17/3462; A61B 17/3468;
(Continued)

(56) References Cited

U.S. PATENT DOCUMENTS 4,531,943 A 7/1985 Tassel et al.
4,710,181 A 12/1987 Fuqua
(Continued)

FOREIGN PATENT DOCUMENTS

EP 1660167 A2 5/2006
WO 2004037333 A1 5/2004
(Continued)

OTHER PUBLICATIONS

International Search Report and Written Opinion dated May 15, 2017 for International Application No. PCT/US2017/020010.
(Continued)

*Primary Examiner* — George J Ulsh
(74) *Attorney, Agent, or Firm* — Seager, Tufte & Wickhem LLP

(57) ABSTRACT

An introducer sheath may include a tubular member comprising an inner layer and an outer layer coaxially disposed about a central longitudinal axis of the introducer sheath, the tubular member being configured to shift between an unexpanded configuration to an expanded configuration. The inner layer may be circumferentially discontinuous along at least a portion of its length. At least a first portion of the inner layer may be configured to move circumferentially relative to the outer layer when shifting between the unexpanded and expanded configurations.

17 Claims, 13 Drawing Sheets

(51) Int. Cl.
  *A61M 39/02* (2006.01)
  *A61F 2/24* (2006.01)
  *A61M 25/00* (2006.01)
  *A61B 17/00* (2006.01)

(52) U.S. Cl.
  CPC ..... *A61B 17/3462* (2013.01); *A61M 25/0662* (2013.01); *A61B 2017/00336* (2013.01); *A61F 2/2427* (2013.01); *A61M 25/0054* (2013.01); *A61M 2025/0024* (2013.01); *A61M 2039/0279* (2013.01)

(58) Field of Classification Search
  CPC ........ A61B 2017/00336; A61M 25/00; A61M 25/06; A61M 25/0662; A61M 2025/0024; A61M 25/0054; A61M 2039/0279; A61F 2/2427
  See application file for complete search history.

(56) References Cited

U.S. PATENT DOCUMENTS

| | | | |
|---|---|---|---|
| 4,738,666 A | 4/1988 | Fuqua | |
| 5,104,388 A | 4/1992 | Quackenbush | |
| 5,176,659 A | 1/1993 | Mancini | |
| 5,320,611 A | 6/1994 | Bonutti et al. | |
| 5,380,304 A | 1/1995 | Parker | |
| 5,489,277 A | 2/1996 | Tolkoff et al. | |
| 5,702,373 A | 12/1997 | Samson | |
| 5,843,027 A * | 12/1998 | Stone ................. | A61F 2/958 604/509 |
| 5,997,508 A | 12/1999 | Lunn et al. | |
| 6,080,141 A | 6/2000 | Castro et al. | |
| 6,090,072 A | 7/2000 | Kratoska et al. | |
| 6,187,000 B1 | 2/2001 | Davison et al. | |
| 6,197,016 B1 | 3/2001 | Fourkas et al. | |
| 6,277,108 B1 | 8/2001 | Mcbroom et al. | |
| 6,358,238 B1 | 3/2002 | Sherry | |
| 6,443,979 B1 | 9/2002 | Stalker et al. | |
| 6,652,492 B1 | 11/2003 | Bell et al. | |
| 6,939,327 B2 | 9/2005 | Hall et al. | |
| 7,144,386 B2 | 12/2006 | Korkor et al. | |
| 7,226,451 B2 | 6/2007 | Shluzas et al. | |
| 7,309,334 B2 | 12/2007 | Von Hoffmann | |
| 7,670,354 B2 | 3/2010 | Davison et al. | |
| 7,713,193 B2 | 5/2010 | Nance et al. | |
| 7,762,995 B2 | 7/2010 | Eversull et al. | |
| 7,766,820 B2 | 8/2010 | Core | |
| 7,837,692 B2 | 11/2010 | Mulholland et al. | |
| 7,837,769 B2 | 11/2010 | Lahr | |
| 7,879,024 B2 | 2/2011 | Thorstenson et al. | |
| 7,892,203 B2 | 2/2011 | Lenker et al. | |
| 7,963,952 B2 | 6/2011 | Wright, Jr. et al. | |
| 8,090,936 B2 | 1/2012 | Fallon et al. | |
| 8,092,481 B2 | 1/2012 | Nance et al. | |
| 8,317,817 B2 | 11/2012 | Davison et al. | |
| 8,690,936 B2 | 4/2014 | Nguyen et al. | |
| 8,744,572 B1 | 6/2014 | Greenhut et al. | |
| 8,764,704 B2 | 7/2014 | Lenker et al. | |
| 8,790,387 B2 | 7/2014 | Nguyen et al. | |
| 9,044,577 B2 | 6/2015 | Bishop et al. | |
| 9,089,669 B2 | 7/2015 | Haslinger et al. | |
| 9,301,840 B2 | 4/2016 | Nguyen et al. | |
| 9,301,841 B2 | 4/2016 | Nguyen et al. | |
| 9,320,508 B2 | 4/2016 | Carroux | |
| 2004/0006344 A1 | 1/2004 | Nguyen et al. | |
| 2004/0087968 A1 | 5/2004 | Core | |
| 2005/0124937 A1 | 6/2005 | Kick et al. | |
| 2005/0125021 A1 | 6/2005 | Nance et al. | |
| 2006/0135981 A1 | 6/2006 | Lenker et al. | |
| 2007/0021768 A1 | 1/2007 | Nance et al. | |
| 2008/0004521 A1 | 1/2008 | Hundley et al. | |
| 2008/0004571 A1 | 1/2008 | Voss | |
| 2008/0200943 A1 | 8/2008 | Barker et al. | |
| 2009/0043285 A1 | 2/2009 | Stehr et al. | |
| 2010/0094392 A1 | 4/2010 | Nguyen et al. | |
| 2010/0198160 A1 | 8/2010 | Voss | |
| 2012/0083877 A1 | 4/2012 | Nguyen et al. | |
| 2012/0323180 A1 | 12/2012 | Chebator et al. | |
| 2013/0066157 A1 | 3/2013 | Guralnik et al. | |
| 2013/0079861 A1 | 3/2013 | Reinert et al. | |
| 2013/0178711 A1 | 7/2013 | Avneri et al. | |
| 2014/0121629 A1 | 5/2014 | MaCaulay et al. | |
| 2014/0236122 A1 | 8/2014 | Anderson et al. | |
| 2015/0238178 A1 | 8/2015 | Carroux | |
| 2016/0030705 A1 | 2/2016 | Fargahi | |
| 2016/0213882 A1 | 7/2016 | Fitterer et al. | |
| 2016/0296332 A1 | 10/2016 | Zhou et al. | |
| 2017/0014156 A1 | 1/2017 | Steffen | |
| 2017/0252062 A1 | 9/2017 | Fitterer et al. | |

FOREIGN PATENT DOCUMENTS

| | | |
|---|---|---|
| WO | 2006069215 A2 | 6/2006 |
| WO | 2010017537 A2 | 2/2010 |

OTHER PUBLICATIONS

International Search Report and Written Opinion dated May 28, 2018 for International Application No. PCT/US2018/017539.
International Search Report and Written Opinion PCT/US2016/014401, dated Jul. 12, 2016.
International Search Report and Written Opinion PCT/US2016/016608, dated Apr. 21, 2016.
International Search Report and Written Opinion dated Jul. 6, 2018 for International Application No. PCT/US2018/032636.

\* cited by examiner

RADIALLY EXPANDABLE INTRODUCER SHEATH

CROSS-REFERENCE TO RELATED APPLICATIONS

This application claims the benefit of priority under 35 U.S.C. § 119 to U.S. Provisional Application Ser. No. 62/506,239, filed May 15, 2017, the entirety of which is incorporated herein by reference.

TECHNICAL FIELD

The present disclosure pertains to medical devices, and methods for manufacturing and/or using medical devices. More particularly, the present disclosure pertains to a radially expandable introducer sheath and/or methods of use and/or manufacture thereof.

BACKGROUND

A wide variety of intracorporeal medical devices have been developed for medical use, for example, surgical and/or intravascular use. In some instances, performing percutaneous medical procedures may require insertion and/or maneuvering of relatively large medical devices through a vasculature. However, inserting the medical device into the vasculature may result in undesirable forces being applied to the vessel walls. For example, as the medical device passes into and/or through the vasculature, it may make undesirable contact with one or more vessel walls. This contact may cause injury to the vessel as the medical device is navigated into calcified or diseased vessels. In some instances, an introducer may be utilized to facilitate the insertion of medical devices into the vessel. Further, vessel trauma resulting from forces applied to the vessel wall by a medical device may be lessened by minimizing the size of an introducer used to access the vessel. Therefore, it may be desirable to design an introducer having a reduced insertion profile, yet capable of expansion when necessary (e.g., during the passage of a medical device therethrough). Of the known medical devices and methods, each has certain advantages and disadvantages. There is an ongoing need to provide alternative medical devices as well as alternative methods for manufacturing and/or using medical devices.

SUMMARY

In a first aspect, an introducer sheath may comprise a tubular member comprising an inner layer and an outer layer coaxially disposed about a central longitudinal axis of the introducer sheath, the tubular member being configured to shift between an unexpanded configuration to an expanded configuration. The inner layer may be circumferentially discontinuous along at least a portion of its length. At least a first portion of the inner layer may be configured to move circumferentially relative to the outer layer when shifting between the unexpanded and expanded configurations.

In addition or alternatively, and in a second aspect, the inner layer includes a plurality of longitudinally-oriented elements.

In addition or alternatively, and in a third aspect, the plurality of longitudinally-oriented elements at least partially circumferentially overlap each other in the unexpanded configuration.

In addition or alternatively, and in a fourth aspect, the plurality of longitudinally-oriented elements circumferentially overlap each other less as the tubular member shifts from the unexpanded configuration toward the expanded configuration.

In addition or alternatively, and in a fifth aspect, the plurality of longitudinally-oriented elements is circumferentially spaced apart from each other in the expanded configuration.

In addition or alternatively, and in a sixth aspect, the outer layer is circumferentially continuous along its entire length.

In addition or alternatively, and in a seventh aspect, the outer layer is formed from a substantially elastic material.

In addition or alternatively, and in an eighth aspect, the outer layer is circumferentially discontinuous along at least a portion of its length.

In addition or alternatively, and in a ninth aspect, further comprising an elastomeric outer sheath disposed about the outer layer of the tubular member.

In addition or alternatively, and in a tenth aspect, the elastomeric outer sheath is disposed against the outer layer of the tubular member.

In addition or alternatively, and in an eleventh aspect, the inner layer is secured to the outer layer such that at least a second portion of the inner layer is circumferentially immovable relative to the outer layer.

In addition or alternatively, and in a twelfth aspect, a medical device system may comprise a replacement heart valve delivery system, and an introducer sheath comprising a tubular member comprising an inner layer and an outer layer coaxially disposed about a central longitudinal axis of the introducer sheath, the tubular member being configured to shift between an unexpanded configuration to an expanded configuration. The inner layer may be circumferentially discontinuous along at least a portion of its length. At least a first portion of the inner layer may be configured to move circumferentially relative to the outer layer when shifting between the unexpanded and expanded configurations. The replacement heart valve delivery system may be configured to slide within a lumen of the introducer sheath for advancement within a vasculature.

In addition or alternatively, and in a thirteenth aspect, the replacement heart valve delivery system includes a replacement heart valve implant.

In addition or alternatively, and in a fourteenth aspect, the replacement heart valve delivery system is unexposed to the vasculature while the replacement heart valve delivery system is disposed within the lumen of the introducer sheath.

In addition or alternatively, and in a fifteenth aspect, the tubular member is configured to shift toward the expanded configuration as the replacement heart valve delivery system passes through the lumen of the introducer sheath and shift toward the unexpanded configuration when the replacement heart valve delivery system is removed from the lumen of the introducer sheath.

In addition or alternatively, and in a sixteenth aspect, a method of delivering a replacement heart valve may comprise: advancing an introducer sheath through a vasculature to an access site, the introducer sheath including a tubular member comprising an inner layer and an outer layer coaxially disposed about a central longitudinal axis of the introducer sheath; inserting a replacement heart valve delivery system into a lumen of the introducer sheath; advancing the replacement heart valve delivery system through the lumen of the introducer sheath to a treatment site, wherein the introducer sheath radially expands as the replacement heart valve delivery system is advanced through the introducer sheath; and deploying the replacement heart valve at the treatment site.

In addition or alternatively, and in a seventeenth aspect, the inner layer is circumferentially discontinuous along at least a portion of its length and at least a first portion of the inner layer is configured to move circumferentially relative to the outer layer when the introducer sheath radially expands as the replacement heart valve delivery system is advanced through the introducer sheath.

In addition or alternatively, and in an eighteenth aspect, the outer layer is circumferentially discontinuous along at least a portion of its length.

In addition or alternatively, and in a nineteenth aspect, the inner layer and the outer layer overlap such that when the introducer sheath radially expands as the replacement heart valve delivery system is advanced through the introducer sheath, the lumen of the introducer sheath remains circumferentially closed to the vasculature.

In addition or alternatively, and in a twentieth aspect, the inner layer and the outer layer are arranged in opposing clamshell configurations.

The above summary of some embodiments, aspects, and/or examples is not intended to describe each embodiment or every implementation of the present disclosure. The figures and the detailed description which follows more particularly exemplify these embodiments.

BRIEF DESCRIPTION OF THE DRAWINGS

The disclosure may be more completely understood in consideration of the following detailed description of various embodiments in connection with the accompanying drawings, in which.

Figure 1:
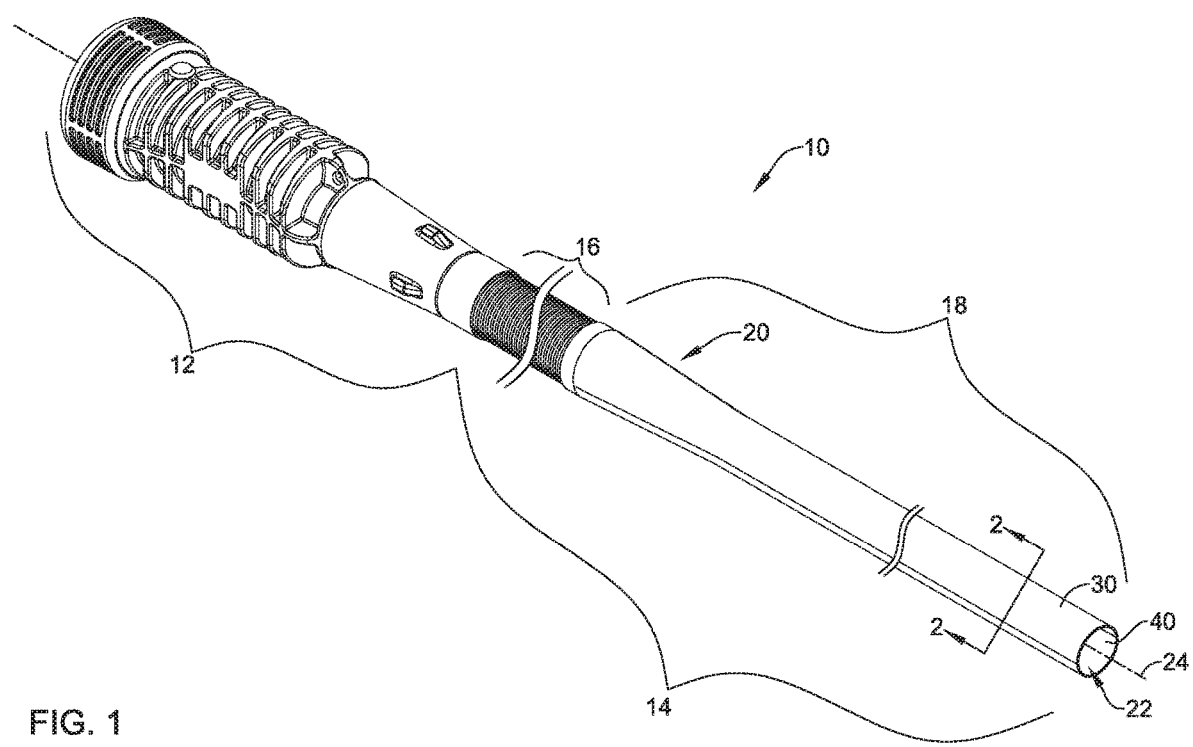
FIG. 1 illustrates an example introducer sheath.

While aspects of the disclosure are amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

The following description should be read with reference to the drawings, which are not necessarily to scale, wherein like reference numerals indicate like elements throughout the several views. The detailed description and drawings are intended to illustrate but not limit the claimed invention. Those skilled in the art will recognize that the various elements described and/or shown may be arranged in various combinations and configurations without departing from the scope of the disclosure. The detailed description and drawings illustrate example embodiments of the claimed invention. However, in the interest of clarity and ease of understanding, while every feature and/or element may not be shown in each drawing, the feature(s) and/or element(s) may be understood to be present regardless, unless otherwise specified.

For the following defined terms, these definitions shall be applied, unless a different definition is given in the claims or elsewhere in this specification.

All numeric values are herein assumed to be modified by the term "about," whether or not explicitly indicated. The term "about", in the context of numeric values, generally refers to a range of numbers that one of skill in the art would consider equivalent to the recited value (e.g., having the same function or result). In many instances, the term "about" may include numbers that are rounded to the nearest significant figure. Other uses of the term "about" (e.g., in a context other than numeric values) may be assumed to have their ordinary and customary definition(s), as understood from and consistent with the context of the specification, unless otherwise specified.

The recitation of numerical ranges by endpoints includes all numbers within that range, including the endpoints (e.g., 1 to 5 includes 1, 1.5, 2, 2.75, 3, 3.80, 4, and 5).

Although some suitable dimensions, ranges, and/or values pertaining to various components, features and/or specifications are disclosed, one of skill in the art, incited by the present disclosure, would understand desired dimensions, ranges, and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise. It is to be noted that in order to facilitate understanding, certain features of the disclosure may be described in the singular, even though those features may be plural or recurring within the disclosed embodiment(s). Each instance of the features may include and/or be encompassed by the singular disclosure(s), unless expressly stated to the contrary. For simplicity and clarity purposes, not all elements of the disclosed invention are necessarily shown in each figure or discussed in detail below. However, it will be understood that the following discussion may apply equally to any and/or all of the components for which there are more than one, unless explicitly stated to the contrary. Additionally, not all instances of some elements or features may be shown in each figure for clarity.

Relative terms such as "proximal", "distal", "advance", "retract", variants thereof, and the like, may be generally considered with respect to the positioning, direction, and/or operation of various elements relative to a user/operator/manipulator of the device, wherein "proximal" and "retract" indicate or refer to closer to or toward the user and "distal" and "advance" indicate or refer to farther from or away from the user. In some instances, the terms "proximal" and "distal" may be arbitrarily assigned in an effort to facilitate understanding of the disclosure, and such instances will be readily apparent to the skilled artisan. Other relative terms, such as "upstream", "downstream", "inflow", and "outflow" refer to a direction of fluid flow within a lumen, such as a body lumen, a blood vessel, or within a device.

The term "extent" may be understood to mean a greatest measurement of a stated or identified dimension, unless the extent or dimension in question is preceded by or identified as a "minimum", which may be understood to mean a smallest measurement of the stated or identified dimension. For example, "outer extent" may be understood to mean a maximum outer dimension, "radial extent" may be understood to mean a maximum radial dimension, "longitudinal extent" may be understood to mean a maximum longitudinal dimension, etc. Each instance of an "extent" may be different (e.g., axial, longitudinal, lateral, radial, circumferential, etc.) and will be apparent to the skilled person from the context of the individual usage. Generally, an "extent" may be considered a greatest possible dimension measured according to the intended usage, while a "minimum extent" may be considered a smallest possible dimension measured according to the intended usage. In some instances, an "extent" may generally be measured orthogonally within a plane and/or cross-section, but may be, as will be apparent from the particular context, measured differently—such as, but not limited to, angularly, radially, circumferentially (e.g., along an arc), etc.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to effect the particular feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

For the purpose of clarity, certain identifying numerical nomenclature (e.g., first, second, third, fourth, etc.) may be used throughout the description and/or claims to name and/or differentiate between various described and/or claimed features. It is to be understood that the numerical nomenclature is not intended to be limiting and is exemplary only. In some embodiments, alterations of and deviations from previously-used numerical nomenclature may be made in the interest of brevity and clarity. That is, a feature identified as a "first" element may later be referred to as a "second" element, a "third" element, etc. or may be omitted entirely, and/or a different feature may be referred to as the "first" element. The meaning and/or designation in each instance will be apparent to the skilled practitioner.

Diseases and/or medical conditions that impact the cardiovascular system are prevalent throughout the world. Some mammalian hearts (e.g., human, etc.) include four heart valves: a tricuspid valve, a pulmonary valve, an aortic valve, and a mitral valve. The purpose of the heart valves is to allow blood to flow through the heart and from the heart into the major blood vessels connected to the heart, such as the aorta and the pulmonary artery, for example. In a normally functioning heart valve, blood is permitted to pass or flow downstream through the heart valve (e.g., from an atrium to a ventricle, from a ventricle to an artery, etc.) when the heart valve is open, and when the heart valve is closed, blood is prevented from passing or flowing back upstream through the heart valve (e.g., from a ventricle to an atrium, etc.). Some relatively common medical conditions may include or be the result of inefficiency, ineffectiveness, or complete failure of one or more of the valves within the heart. Treatment of defective heart valves poses other challenges in that the treatment often requires the repair or outright replacement of the defective valve. Such therapies may be highly invasive to the patient. Disclosed herein are medical devices that may be used within a portion of the cardiovascular system in order to diagnose, treat, and/or repair the system. At least some of the medical devices disclosed herein may include a replacement heart valve (e.g., a replacement aortic valve, a replacement mitral valve, etc.) and may reduce, treat, and/or prevent the occurrence of defects such as (but not limited to) regurgitation, leaflet prolapse, and/or valve stenosis. In addition, the devices disclosed herein may deliver the replacement heart valve percutaneously and, thus, may be much less invasive to the patient, although other surgical methods and approaches may also be used. The devices disclosed herein may also provide a number of additional desirable features and benefits as described in more detail below.

FIG. 1 illustrates an example introducer sheath 10 (e.g., delivery sheath, access sheath, etc.). The introducer sheath 10 may include a tubular member 14 having a proximal end attached to a distal end of a hub member 12. The tubular member 14 may include a proximal section 16 and a distal section 18. The introducer sheath 10, the hub member 12, and/or the tubular member 14 may include and/or define a lumen 22 extending longitudinally through the introducer sheath 10, the hub member 12, and/or the tubular member 14 along and/or coaxial with a central longitudinal axis 24 of the introducer sheath 10.

In some embodiments, the distal section 18 of the tubular member 14 may include a tapered region 20 positioned and/or extending distally of the proximal section 16 of the tubular member 14. In some embodiments, at least a portion of the distal section 18 of the introducer sheath 10 may have a substantially constant outer diameter region extending distally from and/or which transitions into the tapered region 20. At least a portion of tapered region 20 may have an outer diameter which is greater than the outer diameter of the at least a portion of the distal section 18 having the substantially constant outer diameter region extending distally from and/or which transitions into the tapered region 20. However, this is not intended to be limiting. It is contemplated that any portion of the introducer sheath 10 may include any number of tapered portions, constant outer diameter regions, and/or combinations thereof.

In some embodiments, the proximal section 16 of the tubular member 14 may optionally include a spring member. In some examples, a covering may be positioned along and/or be disposed on an outer surface, an inner surface, and/or both the inner and outer surfaces of the spring member. For example, in some embodiments, the spring member may be positioned between (e.g., laminated) an outer covering positioned along and/or disposed on the outer surface of spring member and an inner covering may be positioned along and/or disposed on the inner surface of the spring member.

Additionally, in some embodiments, the hub member 12 may optionally include a hemostatic valve or seal disposed therein. The hemostatic valve or seal may prevent fluid(s) (e.g., blood, etc.) from flowing proximally through the lumen 22 of the introducer sheath 10, the hub member 12, and/or the tubular member 14. In at least some examples, the hub member 12 may include a port in fluid communication with the lumen 22 of the introducer sheath 10, the hub member 12, and/or the tubular member 14.

In some embodiments, the introducer sheath 10 may permit a medical device (e.g., a medical implant, a replacement heart valve delivery system, etc.) to pass through the hub member 12, the proximal section 16, and the distal section 18. In one example, the medical device may pass through the lumen 22 of the introducer sheath 10, the hub member 12, and/or the tubular member 14 while being inserted into a body lumen. For example, the introducer sheath 10 may be configured to radially expand such that the introducer sheath 10 may accommodate and/or pass medical devices which have an outer diameter or maximum outer extent greater than an inner diameter or inner extent of the lumen 22 of the introducer sheath 10, the hub member 12, and/or the tubular member 14.

In at least some embodiments, the tubular member 14 may comprise an inner layer 40 and an outer layer 30 coaxially disposed about the central longitudinal axis 24 of the introducer sheath 10. In some embodiments, at least a portion of an outer surface of the inner layer 40 may be in contact with and/or in engagement with at least a portion of an inner surface of the outer layer 30. In some embodiments, at least a portion of an outer surface of the inner layer 40 may be in sliding contact with and/or in engagement with at least a portion of an inner surface of the outer layer 30. Some suitable but non-limiting materials for the introducer sheath 10, the hub member 12, the tubular member 14, the proximal section 16, the distal section 18, the outer layer 30, and/or the inner layer 40, for example metallic materials, polymer materials, composite materials, etc., are described below.

Figures 2A, 2B, 2C:
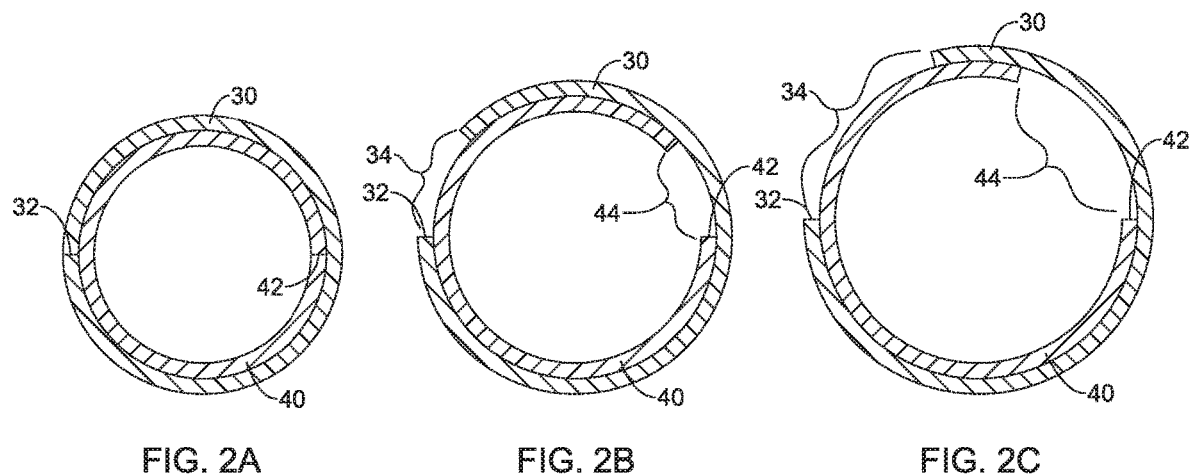
FIG. 2A is a cross-section of the introducer sheath of FIG. 1 in an unexpanded state taken along line 2-2.
FIG. 2B is a cross-section of the introducer sheath of FIG. 1 in a partially expanded state taken along line 2-2.
FIG. 2C is a cross-section of the introducer sheath of FIG. 1 in an expanded state taken along line 2-2.

In some embodiments, the introducer sheath 10, the tubular member 14, and/or the distal section 18 may be configured to shift between an unexpanded configuration, as shown in FIG. 2A for example, a partially expanded configuration (e.g., FIG. 2B), and/or a fully expanded configuration (e.g., FIG. 2C). The skilled person will recognize that the example configurations described immediately above are illustrative only and are not intended to be limiting. As such, in some examples, the configuration shown in FIG. 2B may correspond to a fully expanded configuration and/or the configuration shown in FIG. 2C may correspond to a partially expanded configuration. In some embodiments, the fully expanded configuration may be defined by a maximum outer extent of a medical device being passed through the lumen 22 of the introducer sheath 10, the hub member 12, and/or the tubular member 14. Other configurations and arrangements are also contemplated.

In most examples, the lumen 22 of the introducer sheath 10, the hub member 12, and/or the tubular member 14 is circumferentially closed and/or isolated from any surrounding and/or outside lumen or environment except for the port in the hub member 12 and/or a distal opening at a distalmost end of the lumen 22. As seen in FIGS. 2A-2C, for example, at least a first portion of the inner layer 40 may be configured to move circumferentially relative to the outer layer 30 (or at least a first portion of the outer layer 30 may be configured to move circumferentially relative to the inner layer 40) when shifting between the unexpanded configuration, the partially expanded configuration, and/or the fully expanded configuration, as will be explained in more detail below.

In some embodiments, the inner layer 40 may be circumferentially discontinuous along at least a portion of its length. For example, the inner layer 40 may include a cut 42 (e.g., a slit, a separation, etc.) extending through the inner layer 40. In some embodiments, the outer layer 30 may be circumferentially discontinuous along at least a portion of its length. For example, the outer layer 30 may include a cut 32 (e.g., a slit, a separation, etc.) extending through the outer layer 30. For the purpose of this disclosure, discontinuous may be understood to mean or refer to an element that does not extend in a continuous circumference and/or does not completely surround the relevant or corresponding axis or feature (e.g., the lumen 22, the central longitudinal axis 24). For example, as viewed along the central longitudinal axis 24, the inner layer 40 may develop a gap 44 (e.g., a space, etc.) from one radial point to another radial point, which may be referred to as a gap angle between opposing sides or faces of the cut 42. The inner layer 40 may define a circumferential length around an outer surface of the inner layer 40 between the opposing sides or faces of the cut 42. Similarly, for example, as viewed along the central longitudinal axis 24, the outer layer 30 may develop a gap 34 (e.g., a space, etc.) from one radial point to another radial point, which may be referred to as a gap angle between opposing sides or faces of the cut 32. The outer layer 30 may define a circumferential length around an outer surface of the outer layer 30 between the opposing sides or faces of the cut 32. In some embodiments, the inner layer 40 and/or the outer layer 30 may be arranged in opposing clamshell configurations. For example, as viewed along the central longitudinal axis 24 in FIGS. 2A-2C, the inner layer 40 may open with the gap 44 to the right and the outer layer 30 may open with the gap 34 to the left. This is merely an example, and other configurations and/or arrangements are also possible.

Figure 3:
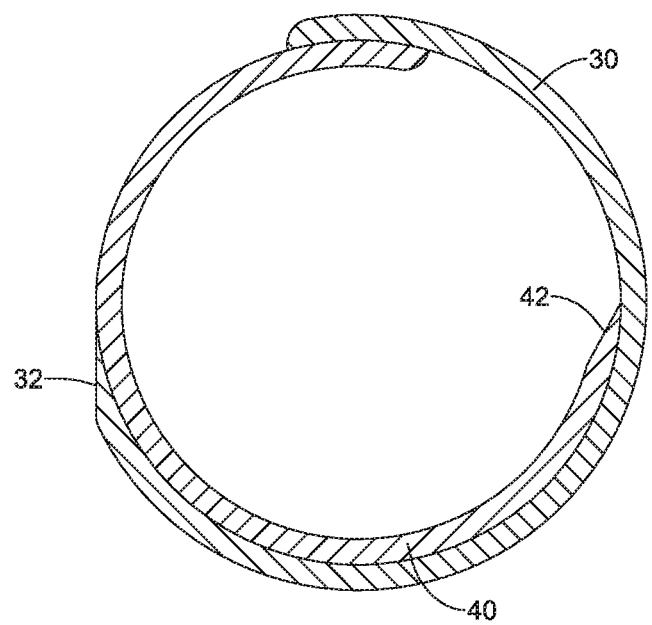
FIG. 3 illustrates a cross-section of an alternative configuration of the introducer sheath of FIG. 1 in an expanded state.

Numerous other configurations, alternative embodiments, and/or additional features are also contemplated. For example, as shown in FIG. 3, the faces of the cut 32 of the outer layer 30 may include rounded, tapered, and/or chamfered corners or edges, and/or the faces of the cut 42 of the inner layer 40 may include rounded, tapered, and/or chamfered corners or edges.

Figure 4:
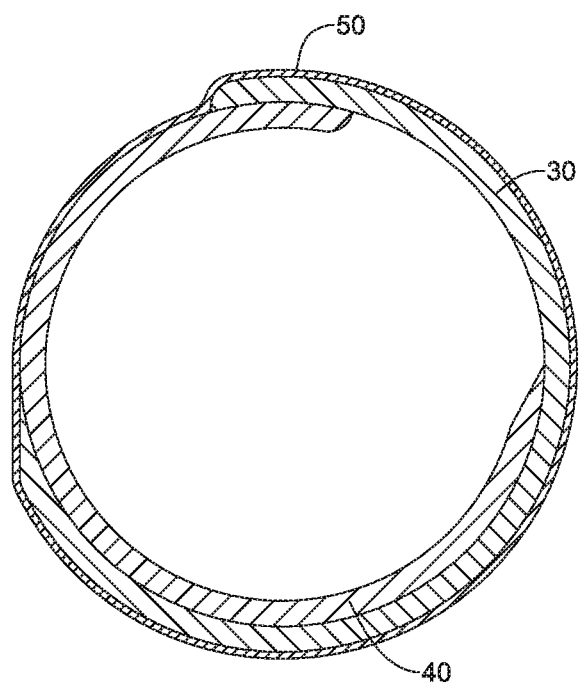
FIG. 4 illustrates a cross-section of an alternative configuration of the introducer sheath of FIG. 1 in an expanded state.

In another example, and as shown in FIG. 4, the tubular member 14 and/or the distal section 18 may include an elastomeric outer sheath 50 disposed on, against, around, and/or about the outer layer 30. The outer sheath 50 may be formed from a substantially elastic material, and may be configured to resiliently radially expand with the tubular member 14 and/or the distal section 18 without compromising its circumferential continuity. In some embodiments, the outer layer 30 may be disposed in sliding contact and/or engagement with the outer sheath 50, and at least a portion of the outer layer 30 may be configured to move circumferentially relative to the outer sheath 50 when shifting between the unexpanded configuration, the partially expanded configuration, and/or the fully expanded configuration. The outer sheath 50 may be included with any configuration of the tubular member 14 and/or the distal section 18 illustrated herein, as well as others, and is not limited only to embodiments having rounded, tapered, and/or chamfered corners or edges of the cut(s) 32/42.

Figure 5A:
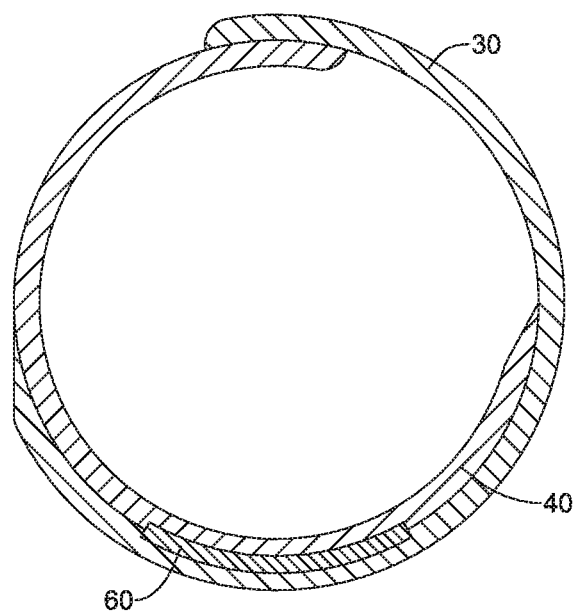
FIG. 5A illustrates a cross-section of an alternative configuration of the introducer sheath of FIG. 1 in an expanded state.
Figure 5B:
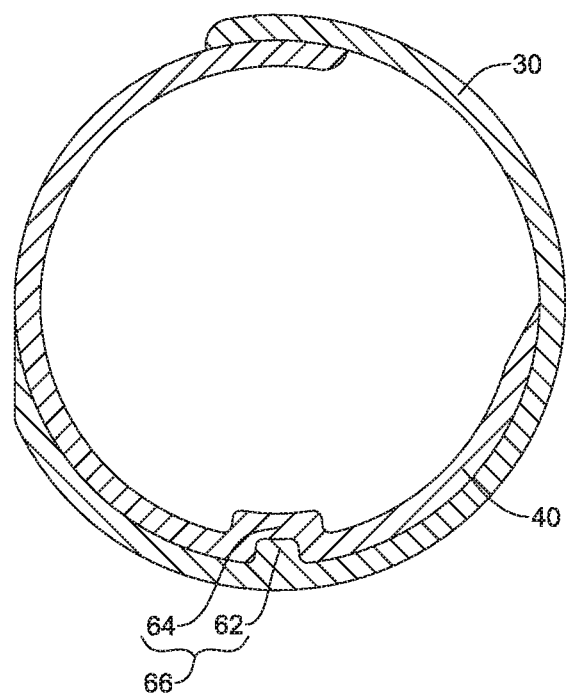
FIG. 5B illustrates a cross-section of an alternative configuration of the introducer sheath of FIG. 1 in an expanded state.

In another example, and as shown in FIGS. 5A and 5B, the inner layer 40 may be secured to the outer layer 30 such that at least a second portion of the inner layer 40 is circumferentially immovable and/or fixed in place relative to the outer layer 30. In the example illustrated in FIG. 5A, a portion of the inner layer 40 may be secured to the outer layer 30 by a bonding agent 60 (e.g., an adhesive, an epoxy, a glue, etc.) configured to fixedly secure and/or attach the inner layer 40 to the outer layer 30. The bonding agent 60 may be included with any configuration of the tubular member 14 and/or the distal section 18 illustrated herein, as well as others, and is not limited only to embodiments having rounded, tapered, and/or chamfered corners or edges of the cut(s) 32/42. In the example illustrated in FIG. 5B, the outer layer 30 includes a projection 62 extending radially inwardly and the inner layer 40 includes a recess 64 configured to receive the projection 62 to form a key structure 66. In at least some embodiments, the projection 62 may be integrally formed with the outer layer 30 as a single structure. In at least some embodiments, the recess 64 may be integrally formed with the inner layer 40 as a single structure. The key structure 66, when the projection 62 is engaged with the recess 64, may secure the inner layer 40 to the outer layer 30 such that at least a second portion of the inner layer 40 is circumferentially immovable and/or fixed in place relative to the outer layer 30. In some embodiments, a mechanical fixation element (e.g., a screw, a rivet, a pin, etc.) may also be used, either in place of or in conjunction with, the bonding agent 60 and/or the key structure 66. The projection 62, the recess 64, and/or the key structure 66 may be included with any configuration of the tubular member 14 and/or the distal section 18 illustrated herein, as well as others, and is not limited only to embodiments having rounded, tapered, and/or chamfered corners or edges of the cut(s) 32/42. Some suitable but non-limiting materials for the projection 62, the recess 64, and/or the key structure 66, for example metallic materials, polymer materials, composite materials, etc., are described below.

In some embodiments, the inner layer 40 and/or the outer layer 30 may be configured to radially expand when subjected to a radially outward force from within the lumen 22. In some embodiments, the inner layer 40 and/or the outer layer 30 may have no radially outward self-bias. For example, the tubular member 14, the distal section 18, the inner layer 40, and/or the outer layer 30 may include no means or mechanism to radially expand and/or open on its own (e.g., absent a radially outward force exerted upon the inner layer 40 from within the lumen 22). Instead, the tubular member 14, the distal section 18, the inner layer 40, and/or the outer layer 30 may require a device (e.g., a medical device, a replacement heart valve delivery system, etc.) to be disposed within the lumen 22 to shift the introducer sheath 10, the tubular member 14, and/or the distal section 18 from the unexpanded configuration toward the partially expanded configuration and/or the fully expanded configuration.

In some embodiments, the inner layer 40 and/or the outer layer 30 may be biased radially inwardly toward the unexpanded configuration. In some embodiments, the inner layer 40 and/or the outer layer 30 may be self-biased radially inwardly toward the unexpanded configuration, and in the absence of any device or force pushing radially outward from within the lumen 22, the tubular member 14 and/or the distal section 18 may radially collapse and/or return to the unexpanded configuration.

In some embodiments, the inner layer 40 and/or the outer layer 30 may be formed from a substantially inelastic material, wherein the inner layer 40 and/or the outer layer 30 are substantially unable to "stretch". For example, when the tubular member 14, the distal section 18, inner layer 40, and/or the outer layer 30 is subjected to a radially outward force from within the lumen 22 and the first portion of the inner layer 40 correspondingly moves (e.g., slides, rotates, etc.) circumferentially relative to the outer layer 30, the circumferential length of the outer layer 30 and/or the inner layer 40 (as measured circumferentially along an outer surface of the outer layer 30 and the inner layer 40, respectively) stays constant while an inner diameter and/or inner extent of the lumen 22, the inner layer 40, and/or the outer layer 30 increases. As such, the inner layer 40 and/or the outer layer 30 may be configured to resiliently flex a small amount sufficient to allow an inner diameter and/or inner extent of the lumen 22, the inner layer 40, and/or the outer layer 30 to increase without stretching the inner layer 40 and/or the outer layer 30 to a larger circumferential length. Described another way, when the tubular member 14, the distal section 18, inner layer 40, and/or the outer layer 30 is subjected to a radially outward force from within the lumen 22 and the first portion of the inner layer 40 correspondingly moves (e.g., slides, rotates, etc.) circumferentially relative to the outer layer 30, the gap 34 and/or the gap angle of the outer layer 30 and the gap 44 and/or the gap angle of the inner layer 40 may increase while the circumferential length around each layer between opposing sides or faces of the cut 32 of the outer layer and the cut 42 of the inner layer remains constant. Similarly, a thickness of a wall of the inner layer 40 extending from an inner surface of the inner layer 40 to an outer surface of the inner layer 40 may remain substantially constant, and a thickness of a wall of the outer layer 30 extending from an inner surface of the outer layer 30 to an outer surface of the outer layer 30 may remain substantially constant, regardless of which configuration (e.g., the unexpanded configuration, the partially expanded configuration, the fully expanded configuration, etc.) the introducer sheath 10, the tubular member 14, and/or the distal section 18 is in.

In embodiments having the outer sheath 50, the outer sheath 50 may be formed from a substantially elastic material, and therefore the outer sheath 50 may be configured to stretch and/or increase its circumferential length as the inner diameter and/or inner extent of the lumen 22 increases. However, in these embodiments, the inner layer 40 and/or the outer layer 30 may function as described above, with the circumferential length of each remaining constant as the inner diameter and/or inner extent of the lumen 22 increases. Some suitable but non-limiting materials for the outer sheath 50, for example metallic materials, polymer materials, composite materials, etc., are described below.

Figure 6:
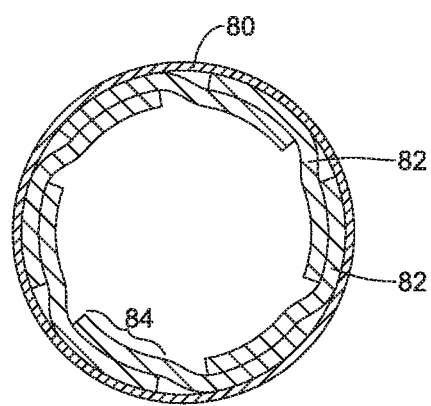
FIG. 6 is a cross-section of an alternative configuration of the introducer sheath of FIG. 1 in an unexpanded state taken along line 2-2.
Figure 7:
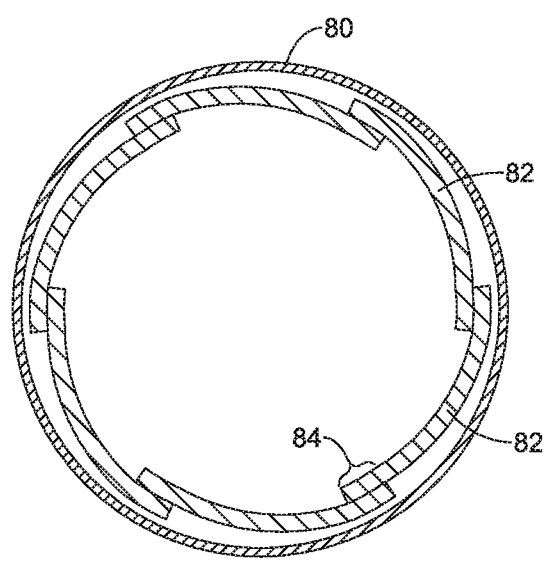
FIG. 7 is a cross-section of the alternative configuration of the introducer sheath of FIG. 6 in a partially expanded state.
Figure 8:
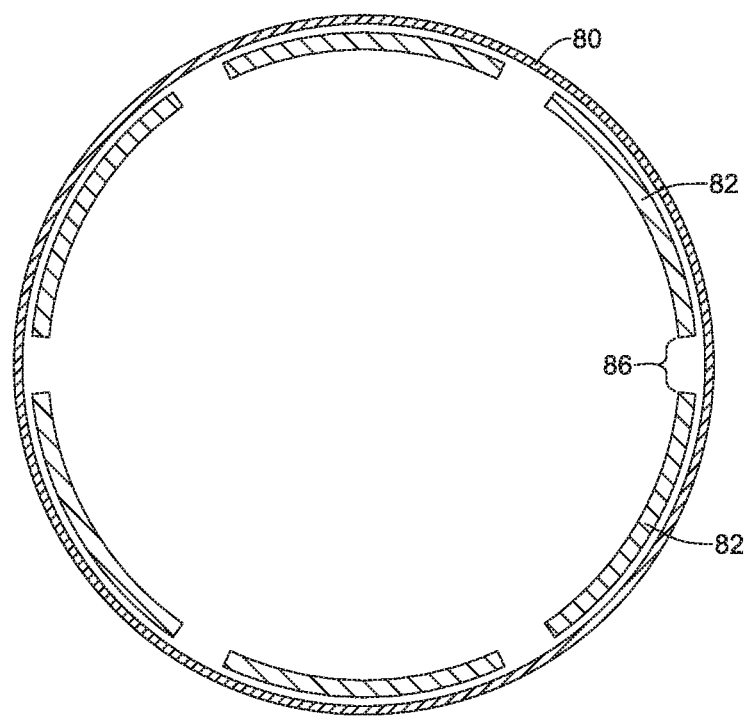
FIG. 8 is a cross-section of the alternative configuration of the introducer sheath of FIG. 6 in an expanded state.

Some aspects of another example configuration of the introducer sheath 10 are shown in FIGS. 6-8. In this example, the tubular member 14 may comprise an inner layer and an outer layer 80 coaxially disposed about the central longitudinal axis 24 of the introducer sheath 10, wherein the introducer sheath 10, the tubular member 14, and/or the distal section 18 is configured to shift between an unexpanded configuration (e.g., FIG. 6), a partially expanded configuration (e.g. FIG. 7), and a fully expanded configuration (e.g., FIG. 8). The inner layer may include a plurality of longitudinally-oriented elements 82, wherein the plurality of longitudinally-oriented elements 82 at least partially circumferentially overlap each other in the unexpanded configuration by an overlap amount 84. The plurality of longitudinally-oriented elements 82 may circumferentially overlap each other less as the tubular member 14 shifts from the unexpanded configuration toward the fully expanded configuration. For example, in the partially expanded configuration, the overlap amount 84 is reduced compared to the unexpanded configuration, as seen in FIG. 7. The plurality of longitudinally-oriented elements 82 may be circumferentially spaced apart from each other by a gap 86 (e.g., a space, etc.) in the fully expanded configuration, as seen in FIG. 8.

In the example configuration of FIGS. 6-8, the outer layer 80 may be circumferentially continuous along its entire length. For example, the outer layer 80 may completely surround the inner layer, the plurality of longitudinally-oriented elements 82, and/or the lumen 22. Accordingly, the outer layer 80 may be formed from a substantially elastic material and therefore the outer layer 80 may be configured to stretch and/or increase its circumferential length (e.g., circumference) as the inner diameter and/or inner extent of the lumen 22 increases and/or as the plurality of longitudinally-oriented elements 82 circumferentially overlap each other less as the tubular member 14 shifts from the unexpanded configuration toward the fully expanded configuration. Some suitable but non-limiting materials for the outer layer 80 and/or the plurality of longitudinally-oriented elements 82, for example metallic materials, polymer materials, composite materials, etc., are described below.

Further, it is contemplated that the inner surface and/or outer surface of the introducer sheath 10, the hub member 12, and/or the tubular member 14 (e.g., the proximal section 16, the distal section 18 and variations of the distal section 18 described herein, the lumen 22, etc.) may include one or more layers and/or coatings, such as a lubricious coating, a hydrophilic coating, a hydrophobic coating, or other suitable coatings, and the like, or may include a lubricant disposed thereon. Some suitable but non-limiting examples of layers and/or coatings are described below.

Figure 9:
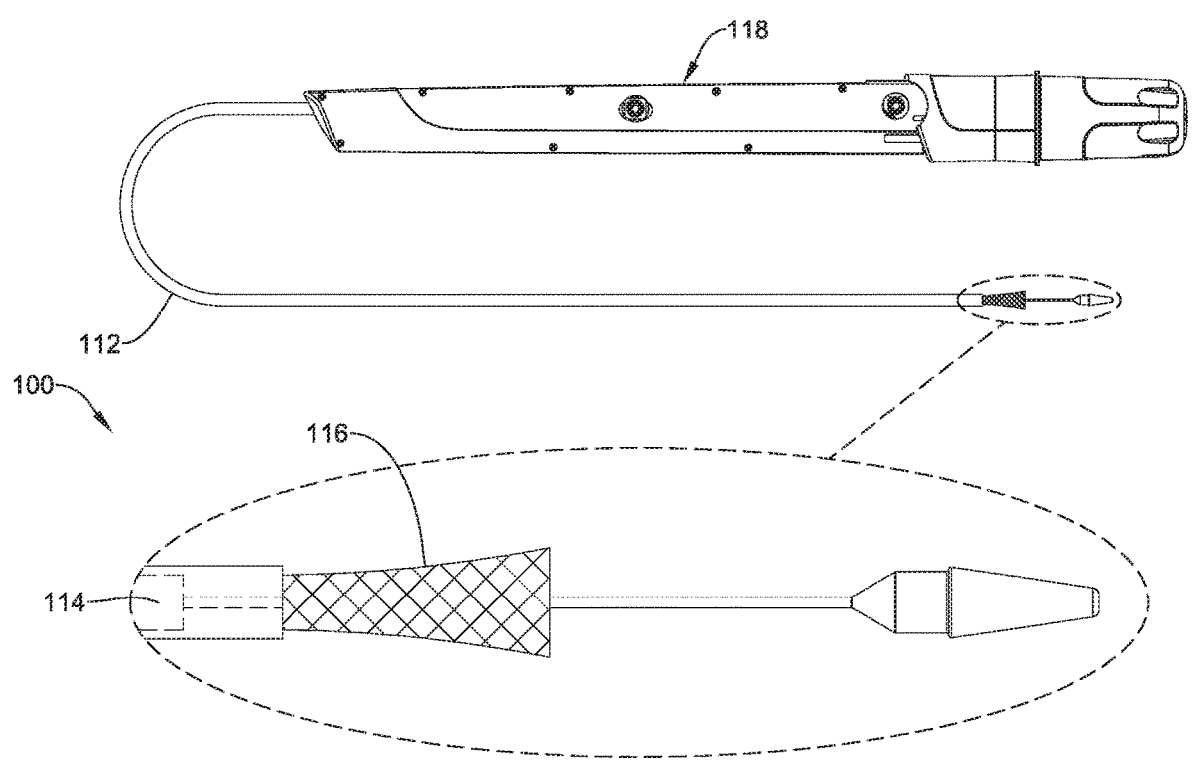
FIG. 9 illustrates an example replacement heart valve delivery system.

FIG. 9 illustrates an example replacement heart valve delivery system 100. Numerous configurations of replacement heart valve delivery systems are contemplated for use with the introducer sheath 10. The exemplary replacement heart valve delivery system 100 includes a delivery sheath 112 having a lumen extending through the delivery sheath 112, and an elongated inner member 114 disposed within the lumen of the delivery sheath 112, wherein the inner member 114 and the delivery sheath 112 are longitudinally slidable relative to each other. A replacement heart valve implant 116 may be disposed within a distal portion of the lumen of the delivery sheath 112 in a collapsed delivery configuration. The replacement heart valve implant 116 may be configured to expand to a deployed configuration when unconstrained by the delivery sheath 112 and/or when actuated to the deployed configuration after releasing the replacement heart valve implant 116 from the delivery sheath 112. The replacement heart valve delivery system 100 may include a handle 118 attached to a proximal end of the delivery sheath 112 and/or the inner member 114. The handle 118 may be operatively connected to the replacement heart valve implant 116 and/or may be configured to actuate the replacement heart valve implant 116 between the collapsed delivery configuration and the deployed configuration. Other configurations are also contemplated, and other medical devices may also be used in connection with the introducer sheath 10.

Figure 10:
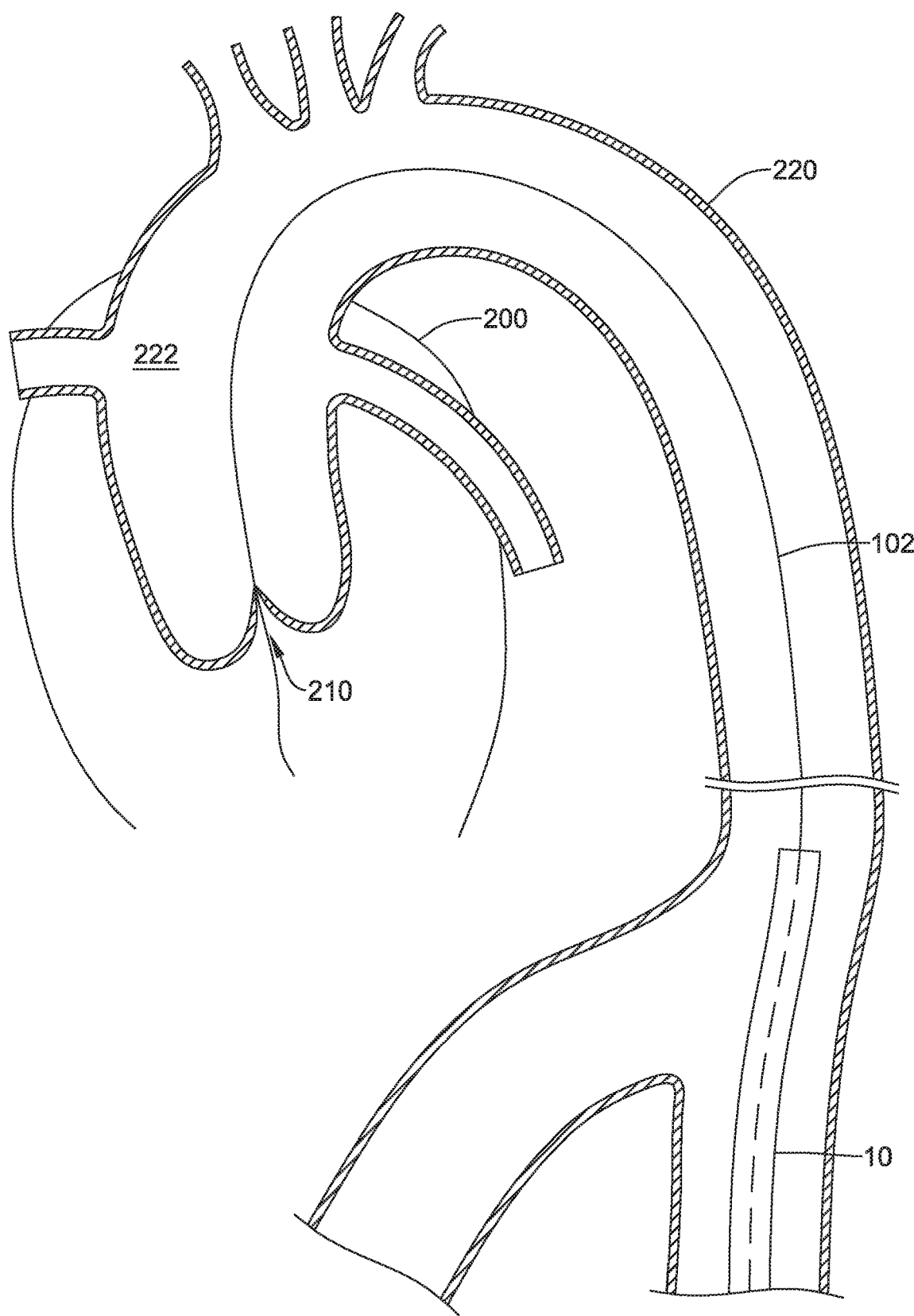
FIGS. 10-12 illustrate the delivery of an example replacement heart valve delivery system using an example introducer sheath of the present application.
Figure 11:
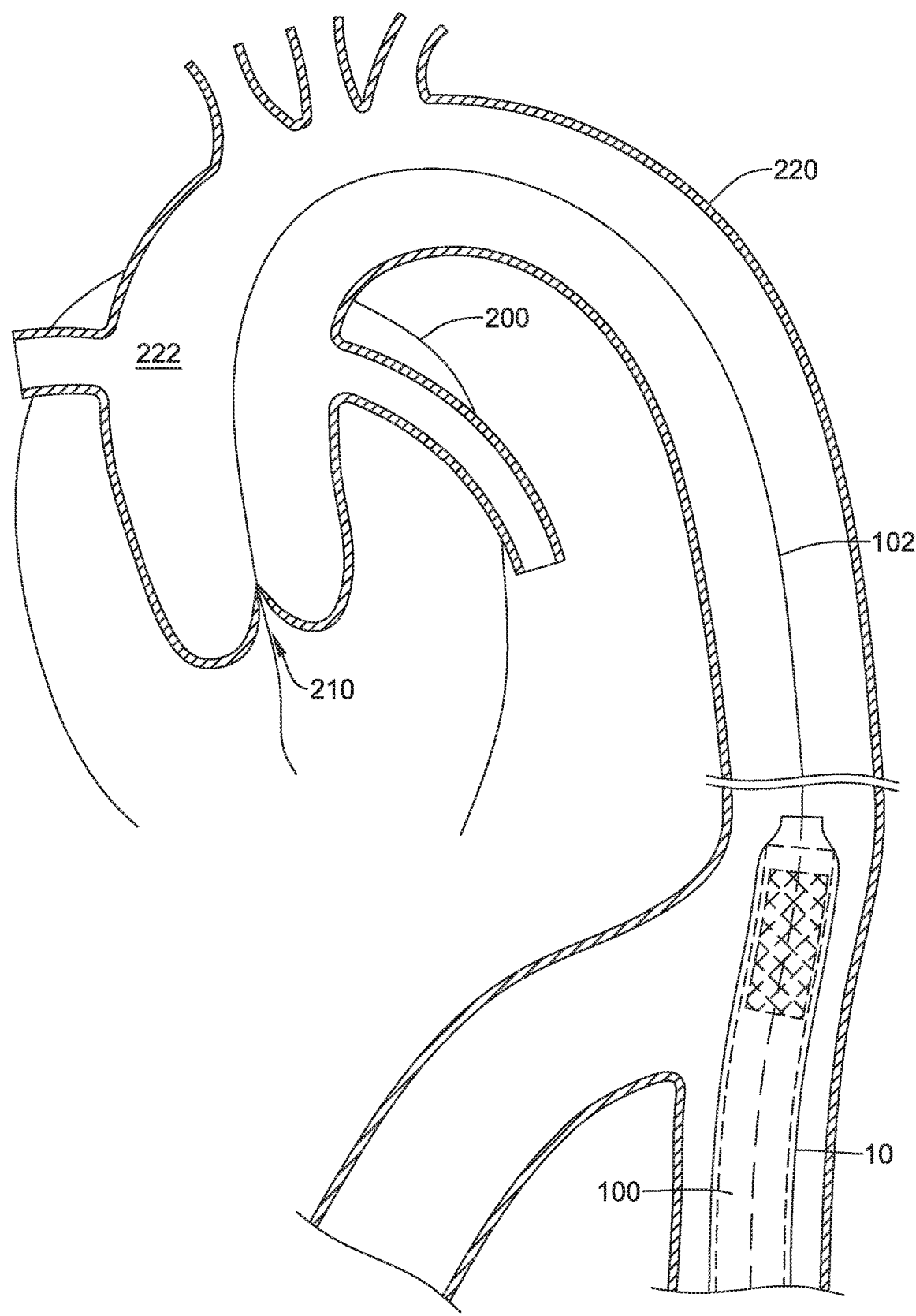
Figure 12:
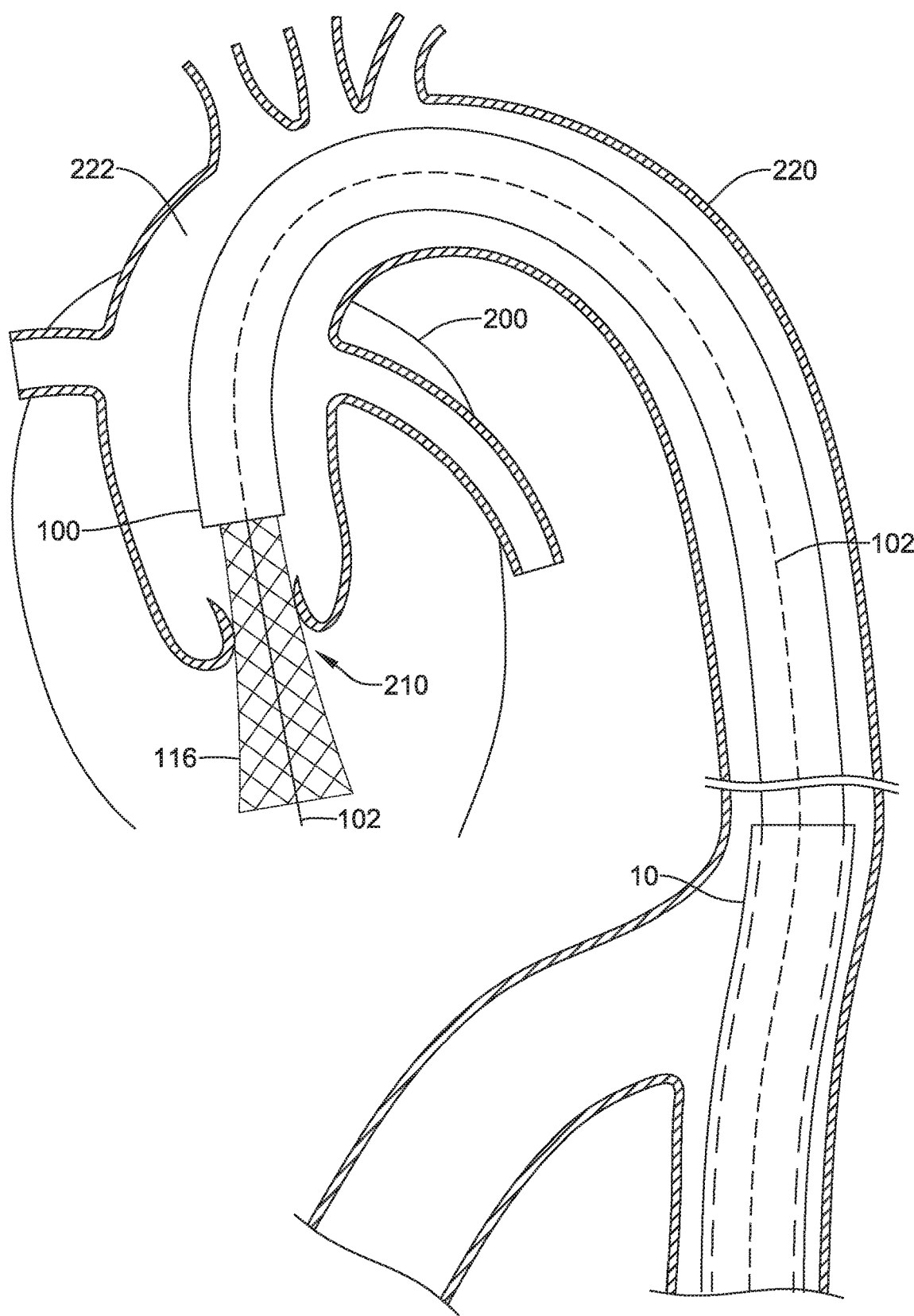

FIGS. 10-12 illustrate aspects of an example method of use of the introducer sheath 10 and/or a medical device system comprising the introducer sheath 10 and the replacement heart valve delivery system 100. In some embodiments, the replacement heart valve delivery system 100 may be configured to slide within the lumen 22 of the introducer sheath 10 for advancement within a vasculature (e.g., an artery, a vein, the aorta 220, the abdominal aorta, the femoral artery, etc.). In some embodiments, a method of delivering a medical device and/or a replacement heart valve may include advancing the introducer sheath 10 through the vasculature (e.g., an artery, a vein, the aorta 220, the abdominal aorta, the femoral artery, etc.) to an access site (e.g., the femoral artery, the common iliac, the abdominal aorta, the aorta 220, the aortic arch 222, etc.) and/or adjacent to a treatment site (e.g., a heart 200, the aortic valve 210, the mitral valve, etc.). For example, in some embodiments, a distal end of the introducer sheath 10 may be positioned within the abdominal aorta and/or in a position superior of the common iliac. In some embodiments, a method of delivering a medical device and/or a replacement heart valve may include advancing the introducer sheath 10 through the vasculature (e.g., an artery, a vein, the aorta 220, the abdominal aorta, the femoral artery, etc.) to the treatment site (e.g., a heart 200, the aortic valve 210, the mitral valve, etc.) and/or adjacent to the treatment site (e.g., a heart 200, the aortic valve 210, the mitral valve, etc.). For example, in some embodiments, the distal end of the introducer sheath 10 may be positioned within the aortic arch 222 or another position further superior of the common iliac than that discussed above.

In some embodiments, the medical device system may include a guidewire 102. In some embodiments, the introducer sheath 10 may be disposed about and/or inserted or advanced over the guidewire 102, as seen in FIG. 10, although the guidewire 102 is not necessarily required in each embodiment. In some embodiments, the guidewire 102 may be inserted and advanced to the treatment site (e.g., the heart 200, the aortic valve 210, the mitral valve, etc.) before the introducer sheath 10 is inserted and/or advanced through the vasculature (e.g., an artery, a vein, the aorta 220, the abdominal aorta, the femoral artery, etc.). In some embodiments, for example when treating the aortic valve 210, the guidewire 102 may be inserted and/or advancing or navigated through the aortic valve 210 and into a left ventricle of the heart 200. The introducer sheath 10 may then be advanced over the guidewire 102 until a distal end of the introducer sheath 10 is positioned at the access site (e.g., the femoral artery, the common iliac, the abdominal aorta, the aorta 220, the aortic arch 222, etc.) and/or adjacent to the treatment site (e.g., a heart 200, the aortic valve 210, the mitral valve, etc.).

The method may include inserting the replacement heart valve delivery system 100 into the lumen 22 of the introducer sheath 10, and advancing the replacement heart valve delivery system 100 through the lumen of the introducer sheath 10 past the access site (e.g., the femoral artery, the common iliac, the abdominal aorta, the aorta 220, the aortic arch 222, etc.) to the treatment site (e.g., the heart 200, the aortic valve 210, the mitral valve, etc.), as seen in FIGS. 11-12 for example. In some embodiments, the replacement heart valve delivery system 100 may be advanced over the guidewire 102. The introducer sheath 10 may radially expand as the replacement heart valve delivery system 100 is advanced through the lumen 22 of the introducer sheath 10. For example, the inner layer 40 may be circumferentially discontinuous along at least a portion of its length and at least the first portion of the inner layer 40 is configured to move circumferentially relative to the outer layer 30 when the introducer sheath 10 radially expands from the unexpanded configuration toward the fully expanded configuration as the replacement heart valve delivery system 100 is advanced through the lumen 22 of the introducer sheath 10.

Regardless of the embodiment of the introducer sheath 10 used, the replacement heart valve delivery system 100 may be and/or remain unexposed to the vasculature (e.g., an artery, a vein, the aorta 220, the abdominal aorta, the femoral artery, etc.) while the replacement heart valve delivery system 100 is disposed within the lumen 22 of the introducer sheath 10 and/or until a portion of the replacement heart valve delivery system 100 is disposed distally of the distal end of the introducer sheath 10. In some embodiments, the inner layer 40 and the outer layer 30 circumferentially overlap such that when the introducer sheath 10 radially expands as the replacement heart valve delivery system 100 is advanced through the lumen 22 of the introducer sheath 10, the lumen 22 of the introducer sheath 10 remains circumferentially closed to the vasculature (e.g., an artery, a vein, the aorta 220, the abdominal aorta, the femoral artery, etc.).

The method may include deploying the replacement heart valve implant 116 at the treatment site (e.g., the heart 200, the aortic valve 210, the mitral valve, etc.), as seen in FIG. 12 for example. In some embodiments, the method may further include retracting the replacement heart valve delivery system 100 into the lumen 22 of the introducer sheath 10 and/or the tubular member 14, and then withdrawing the replacement heart valve delivery system 100 and the introducer sheath 10 from the vasculature (e.g., an artery, a vein, the aorta 220, the abdominal aorta, the femoral artery, etc.) together. In some embodiments, the replacement heart valve delivery system 100 may be retracted into the lumen 22 of the introducer sheath 10 and/or the tubular member 14 and completely withdrawn through the lumen 22 of the introducer sheath 10, the hub member 12, and/or the tubular member 14 before withdrawing and/or removing the introducer sheath 10 from the vasculature (e.g., an artery, a vein, the aorta 220, the abdominal aorta, the femoral artery, etc.).

The materials that can be used for the various components of the introducer sheath 10, the hub member 12, the tubular member 14, the proximal section 16, the distal section 18, the tapered region 20, the outer layer 30, the inner layer 40, the outer sheath 50, the outer layer 80, the plurality of longitudinally-oriented elements 82, the replacement heart valve delivery system 100, the guidewire 102, etc. (and/or other systems or components disclosed herein) and the various elements thereof disclosed herein may include those commonly associated with medical devices. For simplicity purposes, the following discussion makes reference to the introducer sheath 10, the hub member 12, the tubular member 14, the proximal section 16, the distal section 18, the tapered region 20, the outer layer 30, the inner layer 40, the outer sheath 50, the outer layer 80, the plurality of longitudinally-oriented elements 82, the replacement heart valve delivery system 100, the guidewire 102, etc. However, this is not intended to limit the devices and methods described herein, as the discussion may be applied to other elements, members, components, or devices disclosed herein, such as, but not limited to, the coil member, the delivery sheath 112, the inner member 114, the replacement heart valve implant 116, the handle 118, etc. and/or elements or components thereof.

In some embodiments, the introducer sheath 10, the hub member 12, the tubular member 14, the proximal section 16, the distal section 18, the tapered region 20, the outer layer 30, the inner layer 40, the outer sheath 50, the outer layer 80, the plurality of longitudinally-oriented elements 82, the replacement heart valve delivery system 100, the guidewire 102, etc., and/or components thereof may be made from a metal, metal alloy, polymer (some examples of which are disclosed below), a metal-polymer composite, ceramics, combinations thereof, and the like, or other suitable material. Some examples of suitable metals and metal alloys include stainless steel, such as 444V, 444L, and 314LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R44035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R44003 such as ELGILOY®, PHYNOX®, and the like); platinum enriched stainless steel; titanium; platinum; palladium; gold; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear than the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions or all of the introducer sheath 10, the hub member 12, the tubular member 14, the proximal section 16, the distal section 18, the tapered region 20, the outer layer 30, the inner layer 40, the outer sheath 50, the outer layer 80, the plurality of longitudinally-oriented elements 82, the replacement heart valve delivery system 100, the guidewire 102, etc., and/or components thereof, may also be doped with, made of, or otherwise include a radiopaque material. Radiopaque materials are understood to be materials capable of producing a relatively bright image on a fluoroscopy screen or another imaging technique during a medical procedure. This relatively bright image aids a user in determining the location of the introducer sheath 10, the hub member 12, the tubular member 14, the proximal section 16, the distal section 18, the tapered region 20, the outer layer 30, the inner layer 40, the outer sheath 50, the outer layer 80, the plurality of longitudinally-oriented elements 82, the replacement heart valve delivery system 100, the guidewire 102, etc. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the introducer sheath 10, the hub member 12, the tubular member 14, the proximal section 16, the distal section 18, the tapered region 20, the outer layer 30, the inner layer 40, the outer sheath 50, the outer layer 80, the plurality of longitudinally-oriented elements 82, the replacement heart valve delivery system 100, the guidewire 102, etc. to achieve the same result.

In some embodiments, a degree of Magnetic Resonance Imaging (MRI) compatibility is imparted into the introducer sheath 10, the hub member 12, the tubular member 14, the proximal section 16, the distal section 18, the tapered region 20, the outer layer 30, the inner layer 40, the outer sheath 50, the outer layer 80, the plurality of longitudinally-oriented elements 82, the replacement heart valve delivery system 100, the guidewire 102, etc. For example, the introducer sheath 10, the hub member 12, the tubular member 14, the proximal section 16, the distal section 18, the tapered region 20, the outer layer 30, the inner layer 40, the outer sheath 50, the outer layer 80, the plurality of longitudinally-oriented elements 82, the replacement heart valve delivery system 100, the guidewire 102, etc., and/or components or portions thereof, may be made of a material that does not substantially distort the image and create substantial artifacts (e.g., gaps in the image). Certain ferromagnetic materials, for example, may not be suitable because they may create artifacts in an MRI image. The introducer sheath 10, the hub member 12, the tubular member 14, the proximal section 16, the distal section 18, the tapered region 20, the outer layer 30, the inner layer 40, the outer sheath 50, the outer layer 80, the plurality of longitudinally-oriented elements 82, the replacement heart valve delivery system 100, the guidewire 102, etc., or portions thereof, may also be made from a material that the MRI machine can image. Some materials that exhibit these characteristics include, for example, tungsten, cobalt-chromium-molybdenum alloys (e.g., UNS: R44003 such as ELGILOY®, PHYNOX®, and the like), nickel-cobalt-chromium-molybdenum alloys (e.g., UNS: R44035 such as MP35-N® and the like), nitinol, and the like, and others.

In some embodiments, the introducer sheath 10, the hub member 12, the tubular member 14, the proximal section 16, the distal section 18, the tapered region 20, the outer layer 30, the inner layer 40, the outer sheath 50, the outer layer 80, the plurality of longitudinally-oriented elements 82, the replacement heart valve delivery system 100, the guidewire 102, etc., and/or portions thereof, may be made from or include a polymer or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyetherester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, polyurethane silicone copolymers (for example, ElastEon® from Aortech Biomaterials or ChronoSil® from AdvanSource Biomaterials), biocompatible polymers, other suitable materials, or mixtures, combinations, copolymers thereof, polymer/metal composites, and the like. In some embodiments, the sheath can be blended with a liquid crystal polymer (LCP). For example, the mixture can contain up to about 6 percent LCP.

In some embodiments, the introducer sheath 10, the hub member 12, the tubular member 14, the proximal section 16, the distal section 18, the tapered region 20, the outer layer 30, the inner layer 40, the outer sheath 50, the outer layer 80, the plurality of longitudinally-oriented elements 82, the replacement heart valve delivery system 100, the guidewire 102, etc. may include a textile material. Some examples of suitable textile materials may include synthetic yarns that may be flat, shaped, twisted, textured, pre-shrunk or unshrunk. Synthetic biocompatible yarns suitable for use in the present invention include, but are not limited to, polyesters, including polyethylene terephthalate (PET) polyesters, polypropylenes, polyethylenes, polyurethanes, polyolefins, polyvinyls, polymethylacetates, polyamides, naphthalene dicarboxylene derivatives, natural silk, and polytetrafluoroethylenes. Moreover, at least one of the synthetic yarns may be a metallic yarn or a glass or ceramic yarn or fiber. Useful metallic yarns include those yarns made from or containing stainless steel, platinum, gold, titanium, tantalum or a Ni—Co—Cr-based alloy. The yarns may further include carbon, glass or ceramic fibers. Desirably, the yarns are made from thermoplastic materials including, but not limited to, polyesters, polypropylenes, polyethylenes, polyurethanes, polynaphthalenes, polytetrafluoroethylenes, and the like. The yarns may be of the multifilament, mono-filament, or spun-types. The type and denier of the yarn chosen may be selected in a manner which forms a biocompatible and implantable prosthesis and, more particularly, a vascular structure having desirable properties.

In some embodiments, the introducer sheath 10, the hub member 12, the tubular member 14, the proximal section 16, the distal section 18, the tapered region 20, the outer layer 30, the inner layer 40, the outer sheath 50, the outer layer 80, the plurality of longitudinally-oriented elements 82, the replacement heart valve delivery system 100, the guidewire 102, etc. may include and/or be treated with a suitable therapeutic agent. Some examples of suitable therapeutic agents may include anti-thrombogenic agents (such as heparin, heparin derivatives, urokinase, and PPack (dextrophenylalanine proline arginine chloromethylketone)); anti-proliferative agents (such as enoxaparin, angiopeptin, monoclonal antibodies capable of blocking smooth muscle cell proliferation, hirudin, and acetylsalicylic acid); anti-inflammatory agents (such as dexamethasone, prednisolone, corticosterone, budesonide, estrogen, sulfasalazine, and mesalamine); antineoplastic/antiproliferative/anti-mitotic agents (such as paclitaxel, 5-fluorouracil, cisplatin, vinblastine, vincristine, epothilones, endostatin, angiostatin and thymidine kinase inhibitors); anesthetic agents (such as lidocaine, bupivacaine, and ropivacaine); anti-coagulants (such as D-Phe-Pro-Arg chloromethyl keton, an RGD peptide-containing compound, heparin, anti-thrombin compounds, platelet receptor antagonists, anti-thrombin antibodies, anti-platelet receptor antibodies, aspirin, prostaglandin inhibitors, platelet inhibitors, and tick antiplatelet peptides); vascular cell growth promoters (such as growth factor inhibitors, growth factor receptor antagonists, transcriptional activators, and translational promoters); vascular cell growth inhibitors (such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin); cholesterol-lowering agents; vasodilating agents; and agents which interfere with endogenous vasoactive mechanisms.

It should be understood that this disclosure is, in many respects, only illustrative. Changes may be made in details, particularly in matters of shape, size, and arrangement of steps without exceeding the scope of the invention. This may include, to the extent that it is appropriate, the use of any of the features of one example embodiment being used in other embodiments. The invention's scope is, of course, defined in the language in which the appended claims are expressed.

What is claimed:

1. An introducer sheath, comprising:
a tubular member comprising an inner layer and an outer layer coaxially disposed about a central longitudinal axis of the introducer sheath, the tubular member being configured to shift between an unexpanded configuration to an expanded configuration;
wherein the inner layer is circumferentially discontinuous along at least a portion of its length;
wherein at least a first portion of the inner layer is configured to slide circumferentially relative to the outer layer when shifting between the unexpanded and expanded configurations;
wherein the outer layer is circumferentially continuous along its entire length;
wherein the inner layer is formed from a substantially inelastic material.

2. The introducer sheath of claim 1, wherein the inner layer includes a plurality of longitudinally-oriented elements.

3. The introducer sheath of claim 2, wherein the plurality of longitudinally-oriented elements at least partially circumferentially overlap each other in the unexpanded configuration.

4. The introducer sheath of claim 3, wherein the plurality of longitudinally-oriented elements circumferentially overlap each other less as the tubular member shifts from the unexpanded configuration toward the expanded configuration.

5. The introducer sheath of claim 2, wherein the plurality of longitudinally-oriented elements is circumferentially spaced apart from each other in the expanded configuration.

6. The introducer sheath of claim 1, wherein the outer layer is formed from a substantially elastic material.

7. The introducer sheath of claim 1, further comprising an elastomeric outer sheath disposed about the outer layer of the tubular member.

8. The introducer sheath of claim 7, wherein the elastomeric outer sheath is disposed against the outer layer of the tubular member.

9. The introducer sheath of claim 1, wherein the inner layer is secured to the outer layer such that at least a second portion of the inner layer is circumferentially immovable relative to the outer layer.

10. A medical device system, comprising:
a replacement heart valve delivery system; and
an introducer sheath comprising a tubular member comprising an inner layer and an outer layer coaxially disposed about a central longitudinal axis of the introducer sheath, the tubular member being configured to shift between an unexpanded configuration to an expanded configuration;
wherein the inner layer is circumferentially discontinuous along at least a portion of its length;
wherein at least a first portion of the inner layer is configured to slide circumferentially relative to the outer layer when shifting between the unexpanded and expanded configurations;

wherein the outer layer is circumferentially continuous along its entire lengths wherein the inner layer is formed from a substantially inelastic material; wherein the replacement heart valve delivery system is configured to slide within a lumen of the introducer sheath for advancement within a vasculature.

11. The medical device system of claim 10, wherein the replacement heart valve delivery system includes a replacement heart valve implant.

12. The medical device system of claim 10, wherein the replacement heart valve delivery system is unexposed to the vasculature while the replacement heart valve delivery system is disposed within the lumen of the introducer sheath.

13. The medical device system of claim 10, wherein the tubular member is configured to shift toward the expanded configuration as the replacement heart valve delivery system passes through the lumen of the introducer sheath and shift toward the unexpanded configuration when the replacement heart valve delivery system is removed from the lumen of the introducer sheath.

14. A method of delivering a replacement heart valve, comprising:
  advancing an introducer sheath through a vasculature to an access site, the introducer sheath including a tubular member comprising an inner layer and an outer layer coaxially disposed about a central longitudinal axis of the introducer sheath;
  the tubular member being configured to shift between an unexpanded configuration to an expanded configuration; wherein the inner layer is circumferentially discontinuous along at least a portion of its length;
  wherein at least a first portion of the inner layer is configured to slide circumferentially relative to the outer layer when shifting between the unexpanded and expanded configurations; wherein the outer layer is circumferentially continuous along its entire lengths wherein the inner layer is formed from a substantially inelastic material;
  inserting a replacement heart valve delivery system into a lumen of the introducer sheath;
  advancing the replacement heart valve delivery system through the lumen of the introducer sheath to a treatment site;
  wherein the introducer sheath radially expands as the replacement heart valve delivery system is advanced through the introducer sheath; and
  deploying the replacement heart valve at the treatment site.

15. The method of claim 14, wherein the outer layer is circumferentially discontinuous along at least a portion of its length.

16. The method of claim 15, wherein the inner layer and the outer layer overlap such that when the introducer sheath radially expands as the replacement heart valve delivery system is advanced through the introducer sheath, the lumen of the introducer sheath remains circumferentially closed to the vasculature.

17. The method of claim 16, wherein the inner layer and the outer layer are arranged in opposing clamshell configurations.

* * * * *